(12) United States Patent
Akerfeldt

(10) Patent No.: US 9,585,645 B2
(45) Date of Patent: Mar. 7, 2017

(54) INSERTION TOOL FOR A MEDICAL CLOSURE DEVICE

(71) Applicant: ST. JUDE MEDICAL COORDINATION CENTER BVBA, Zaventem (BE)

(72) Inventor: Dan Akerfeldt, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 337 days.

(21) Appl. No.: 14/154,900

(22) Filed: Jan. 14, 2014

(65) Prior Publication Data

US 2014/0128911 A1    May 8, 2014

Related U.S. Application Data

(63) Continuation of application No. 11/987,563, filed on Nov. 30, 2007, now Pat. No. 8,652,166.

(51) Int. Cl.
*A61B 17/00* (2006.01)
*A61B 17/34* (2006.01)
*A61B 17/04* (2006.01)

(52) U.S. Cl.
CPC ...... *A61B 17/0057* (2013.01); *A61B 17/3468* (2013.01); *A61B 2017/00575* (2013.01); *A61B 2017/00606* (2013.01); *A61B 2017/00615* (2013.01); *A61B 2017/00623* (2013.01); *A61B 2017/00659* (2013.01); *A61B 2017/00663* (2013.01); *A61B 2017/0496* (2013.01)

(58) Field of Classification Search
CPC A61B 2017/00672; A61B 2017/00606; A61B 2017/00623; A61B 2017/00637; A61B 2017/00641; A61B 2017/00575; A61B 17/0057; A61B 2017/00367; A61M 31/007; A61M 37/0069
USPC .............................................. 604/164.12, 63
See application file for complete search history.

(56) References Cited

U.S. PATENT DOCUMENTS

| 4,990,136 A | * | 2/1991 | Geria ................. A61M 31/007 604/59 |
| 5,021,059 A | | 6/1991 | Kensey et al. |
| 5,284,479 A | * | 2/1994 | de Jong ............ A61M 37/0069 604/130 |
| 5,324,306 A | | 6/1994 | Makower et al. |

(Continued)

FOREIGN PATENT DOCUMENTS

| EP | 1 266 626 B1 | 1/2005 |
| WO | WO 99/22646 A1 | 5/1999 |
| WO | WO 2005/039419 A1 | 5/2005 |

*Primary Examiner* — Christopher L Templeton
(74) *Attorney, Agent, or Firm* — Foley & Lardner LLP

(57) ABSTRACT

An insertion tool for a medical closure device for the sealing of an opening in a wall of a bodily organ includes a tamping force source adapted to deliver a first member to a position at the opening on one side of the wall subsequently to a second member being positioned at the opening on the opposite side of the wall. The tamping force source, which is energized prior to the tamping procedure, can be a spring, an elastic band or a pressurized gas container. A tamping spring can be compressed or extended upon loading. The tamping force source can be released in response to a manual operation or be triggered by retraction of the insertion tool.

24 Claims, 5 Drawing Sheets

(56) References Cited

U.S. PATENT DOCUMENTS

| | | |
|---|---|---|
| 5,649,959 A | 7/1997 | Hannam et al. |
| 5,666,710 A | 9/1997 | Weber et al. |
| 6,063,085 A | 5/2000 | Tay et al. |
| 6,425,911 B1 | 7/2002 | Akerfeldt et al. |
| 6,508,828 B1 | 1/2003 | Akerfeldt et al. |
| 6,860,895 B1* | 3/2005 | Akerfeldt ............ A61B 17/0057 606/139 |
| 6,929,655 B2 | 8/2005 | Egnelov et al. |
| 7,250,057 B2 | 7/2007 | Forsberg |
| 8,088,144 B2 | 1/2012 | Ginn et al. |
| 8,118,831 B2 | 2/2012 | Egnelov et al. |
| 2001/0003158 A1 | 6/2001 | Kensey et al. |
| 2003/0060846 A1 | 3/2003 | Egnelov et al. |
| 2004/0267308 A1 | 12/2004 | Bagaoisan et al. |
| 2005/0033329 A1 | 2/2005 | Bombard et al. |
| 2005/0085773 A1 | 4/2005 | Forsberg |
| 2005/0085851 A1 | 4/2005 | Fiehler et al. |
| 2005/0101967 A1* | 5/2005 | Weber .................... A61F 2/167 606/107 |
| 2006/0229673 A1 | 10/2006 | Forsberg |
| 2006/0229674 A1 | 10/2006 | Forsberg |
| 2006/0265007 A1 | 11/2006 | White et al. |
| 2006/0265008 A1 | 11/2006 | Maruyama et al. |
| 2007/0010829 A1 | 1/2007 | Nobles et al. |
| 2007/0032823 A1 | 2/2007 | Tegg |
| 2007/0225756 A1 | 9/2007 | Preinitz et al. |
| 2007/0239188 A1 | 10/2007 | Boozer et al. |
| 2007/0260250 A1 | 11/2007 | Wisnewski et al. |
| 2008/0065121 A1* | 3/2008 | Kawaura ............ A61B 17/0057 606/146 |

\* cited by examiner

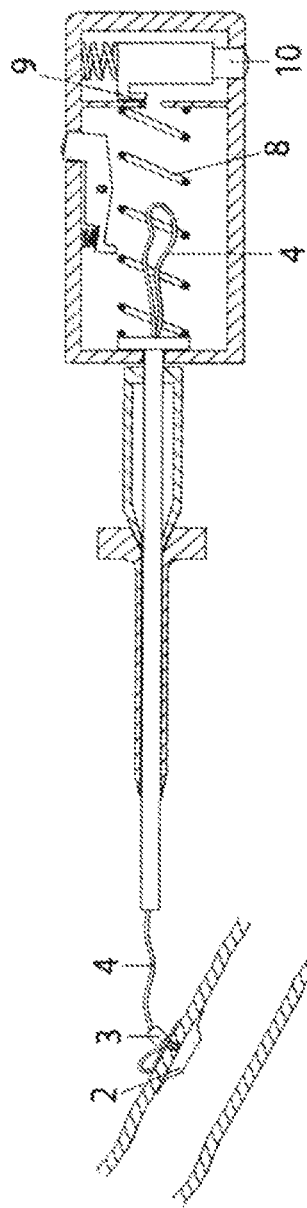
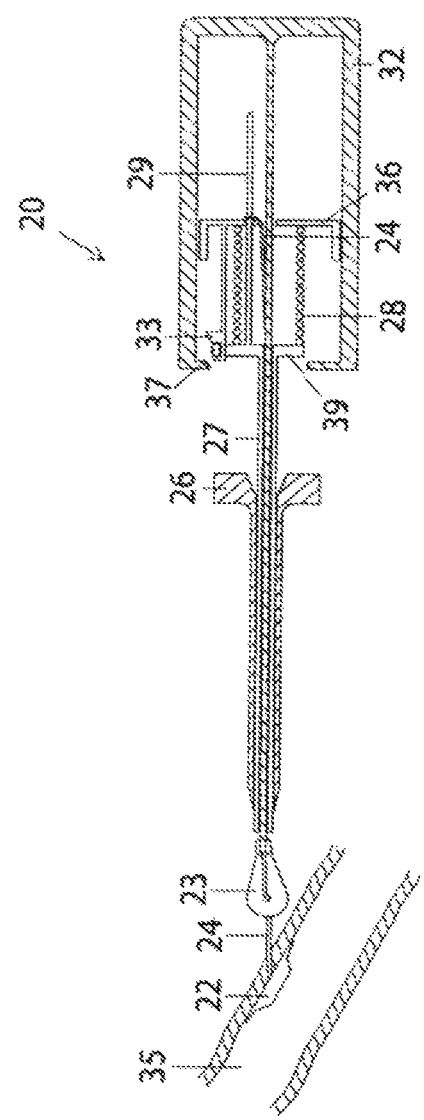
Fig.5
Fig.6

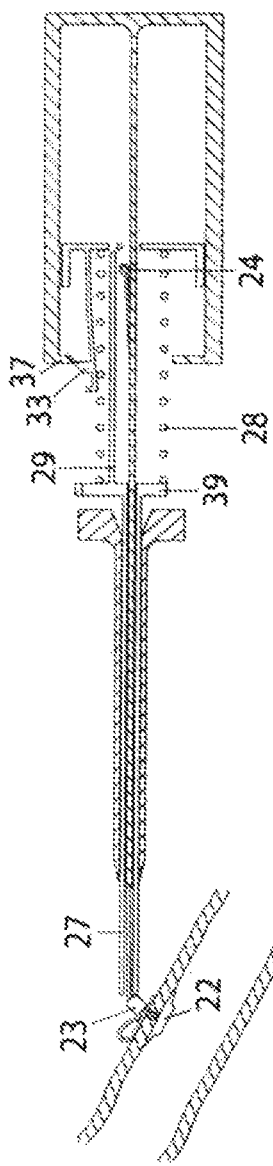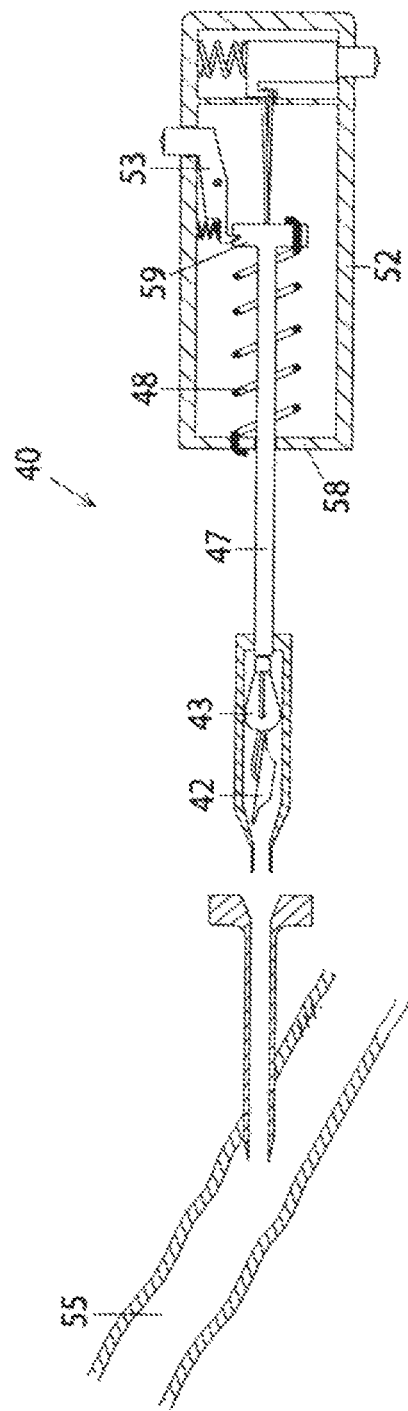

INSERTION TOOL FOR A MEDICAL CLOSURE DEVICE

CROSS-REFERENCE TO RELATED APPLICATIONS

This application is a continuation of U.S. application Ser. No. 11/987,563, filed Nov. 30, 2007, now U.S. Pat. No. 8,652,166, the entire contents of all of which are incorporated herein by reference.

FIELD OF THE INVENTION

The present invention relates generally to an insertion tool to be used together with a medical device in the closure of an opening in a bodily organ, and more particularly to an insertion tool to be used together with a closure device in the sealing of a percutaneous puncture in a vessel, the insertion tool being provided with an improved tamping mechanism comprising an energized tamping force source.

BACKGROUND OF THE INVENTION

During certain types of medical surgery or treatment, an introducer is used to access the vascular system of a patient. The introducer is inserted through the wall of a blood vessel in order to obtain access to the vascular system and may thereafter be used for guiding medical instruments such as catheters, guide wires and the like.

After completion of the medical procedure, there will be an incision or a wound in the wall of the blood vessel corresponding to the size of the introducer. The bleeding from the wound, which is a result of such a surgical operation, can be stopped by applying direct pressure on the wound. However, applying direct pressure on the wound will require assistance of medical personnel and may also restrict the flow of blood through the vessel.

In the U.S. Pat. No. 6,508,828, which is assigned to the present assignee, a sealing device is disclosed for sealing a puncture hole in a vessel wall. The sealing device comprises an inner sealing member, an outer member, and a retaining member. The inner sealing member is adapted to be positioned adjacent to the puncture hole on the inside of a vessel, while the outer member is adapted to be positioned adjacent to the opening on the outside of the vessel. To achieve this, the inner member is deployed inside the vessel, thereafter the assembly is retracted so that the inner member is adjacent to the puncture, and subsequently, the outer member is deployed outside the vessel and thereafter tamped down against the vessel puncture. Thus, the inner and outer members sandwich the vessel wall, and are held together by the retaining member to thereby seal the puncture hole in the vessel wall. The retaining member and the outer member are here held in place by friction acting between the retaining member and the outer member.

An improved tamping mechanism is described in U.S. Pat. No. 6,929,655 and European Patent No. EP 1 266 626, which are assigned to the present assignee. Here, the two functional operations of retracting a pusher used to deploy the inner seal in a vessel and subsequently advancing the outer seal with a tamping tube are combined into a single manual operation. In addition, a third step of releasing a thread, which is used to hold the inner and outer seals together, from a holder, can be included in the single manual step.

Other examples of similar devices include those described in U.S. Pat. No. 7,250,057 and U.S. Patent Publication Nos. 2006/0229674 and 2007/0032823, in which a tissue puncture closure device comprises different types of tamping systems, all of which use the motive force applied when retracting the device and subsequently convert this into a tamping force to tamp a sealing plug against the outer side of a vessel puncture. In this procedure the force of tamping originates at the vessel puncture site, thereby exerting strain on the vessel wall. Depending on the amount of force applied, this could potentially rupture the vessel further, leading to an opposite effect of that which is desired, specifically, additional bleeding and further health risks for the patient.

SUMMARY OF THE INVENTION

There is a need to further ensure optimal closure of the puncture each time a closure device is used and, additionally, to simplify the procedure in terms of the number and complexity of the steps required of the user in deploying the closure device.

The present invention comprises an insertion tool for a medical device for the closure of an opening in a bodily organ, such as a puncture hole in a vessel wall or a septal defect. In the closure procedure, a first and a second closure member are brought together to positions adjacent to the opening and on opposite sides of the wall. A tamping mechanism tamps the two members against opposing sides of the opening, effectively sealing the opening. The tamping is performed using a predefined amount of tamping force, generated by a tamping force source such as a loaded spring, an elastic band or a pressurized gas container. When the tamping force source is a spring, the spring can either be compressed or extended upon loading, and retained in such a configuration until released. The tamping force can be released in response to a manual operation or be automatic.

BRIEF DESCRIPTION OF THE DRAWINGS

FIGS. 1-5 illustrate one embodiment of the present invention.

FIGS. 6 and 7 illustrate a second embodiment of the present invention.

FIG. 8 illustrates a third embodiment of the present invention.

DETAILED DESCRIPTION OF PREFERRED EMBODIMENTS

Figure 1:
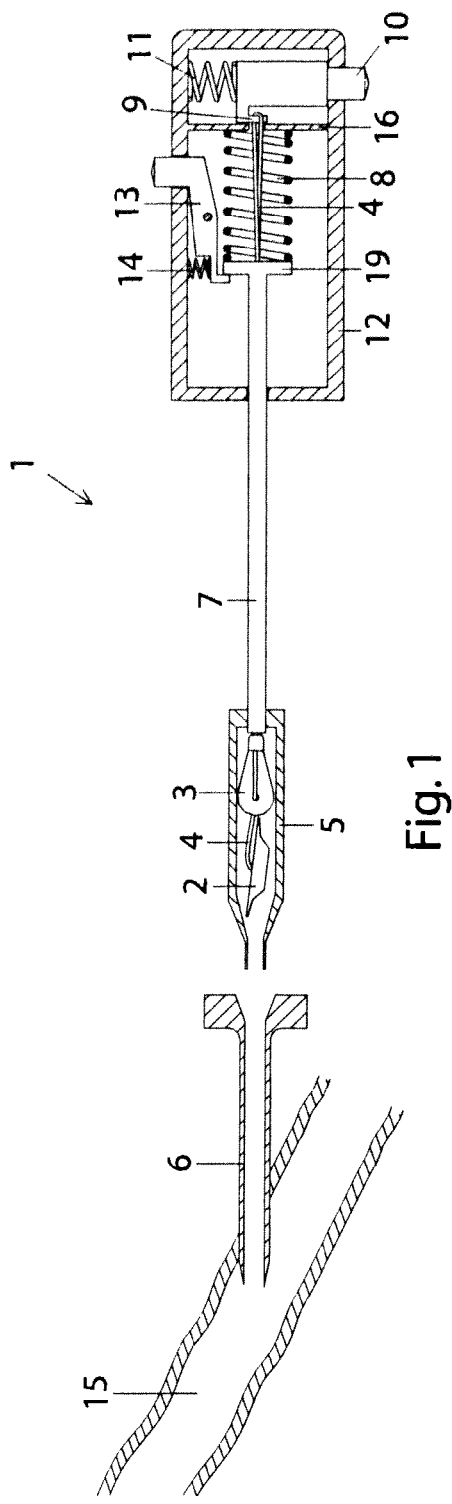

The insertion tool of the present invention is adapted to be used with a medical device for closure of an opening in a bodily organ, such as a blood vessel puncture or a septal defect, where the closure device comprises a first and a second member adapted to be retained in positions adjacent to the opening and on opposite sides of the wall (further described below). In order to overcome the risk of applying too much strain on e.g. the vessel wall when tamping a closure device at a puncture site, the present invention provides a mechanism wherein the amount of force used for tamping of a closure device is not dependent on a considerable force being applied to the vessel wall. Additionally, the tamping force is of a predetermined magnitude, and is prompted either by the user, or by an automatic trigger.

For clarity, the present invention will be described in conjunction with a closure device for sealing of a blood vessel puncture, comprising an inner sealing disc, an outer member and a retaining filament. However, the tamping mechanism of the present invention can be applied to a variety of closure methods that involve bringing together a first and second closure member to positions on opposite sides of a wall of the bodily organ and adjacent to an opening in the wall, and thereafter clamping, tamping or simply moving the two members together to hold the device in place. Therefore, it should be noted that it is within the scope of the invention to apply the present invention on other types of closure devices for blood vessel punctures than that described below, or for the closure of other openings, such as a septal defect in the heart.

The insertion tool of the present invention comprises a tamping mechanism with a tamping force source adapted to be energized prior to initiation of the tamping procedure. The term tamping force source comprises any energy source capable of generating a motive force when released. One example is a compressed or extended spring, which will be described in detail below. Another example is one or more elastic bands, or any other elastic material capable of being compressed and/or extended or expanded, and which will produce motive energy upon release. The term energize indicates, in these cases, either compression or expansion of the spring or elastic material. A third example is using a pressurized container of gas, such as air, carbon dioxide or nitrogen. Here the term energizing implies filling the container with gas to a pressure higher than that of the surrounding space. Those skilled in the art will realize that other means of mechanically accumulating and releasing a predetermined amount of energy are also possible, in order so create a tamping force source with appropriate properties.

One type of closure device that can be used in conjunction with the tamping mechanism of the present invention is a closure device mainly designed for the sealing of a blood vessel puncture and which comprises an inner disc-shaped member, a flat outer member, and a retaining member such as a suture or filament attached to the inner member. The suture is supplied with an enlarged portion adjacent to the inner member and is threaded through the outer member, in order to hold the two members together by frictional forces acting between the suture and the outer member when sandwiching the vessel wall. Alternatively, the two members can be held together by other means, such as a snap-lock acting between the inner and outer members or a knot on the suture. It is also within the scope of the present invention to be applied to insertion of closure devices that comprise umbrella- or disc-shaped plug members that attach to each other via a stem protruding from one of the members, or those devices which comprise an inner anchor member, an outer member in the form of a haemostatic collagen plug or sponge and a filament attached to the inner anchor.

One embodiment of an insertion tool 1 for a closure device is illustrated in FIG. 1. The closure device is here shown as an inner sealing disc 2 and an outer member 3, connected via a filament 4, all initially disposed within a distal housing 5 of the insertion tool 1. The insertion tool 1 is here illustrated to be used with a pre-placed introducer 6, but can also comprise a dedicated introducer. In such a case the user replaces the introducer used in the preceding procedure, positioned to access the interior of a blood vessel 15, with the dedicated introducer prior to the initiation of the closure procedure. The filament 4 is threaded through a tamping tube 7 past or through a tamping spring 8 and attached via a loop to a hook 9. The hook 9 is functionally coupled to a release button 10, which is initially biased by a release spring 11, which in turn maintains the hook 9 in a position to hold on to the filament 4. The tamping tube 7 is slidably mounted within the insertion tool 1 for movement from a retracted position to an advanced position. The tamping spring 8 is mounted between the proximal enlarged end 19 of the tamping tube 7 and an inner proximal ledge 16 of a proximal housing 12. Initially the tamping spring 8 is compressed, i.e. energized. A tamping button 13 holds the tamping spring 8 in place due to the bias of a tamping button spring 14. The tamping spring 8 will be discussed more in detail below.

Figure 2:
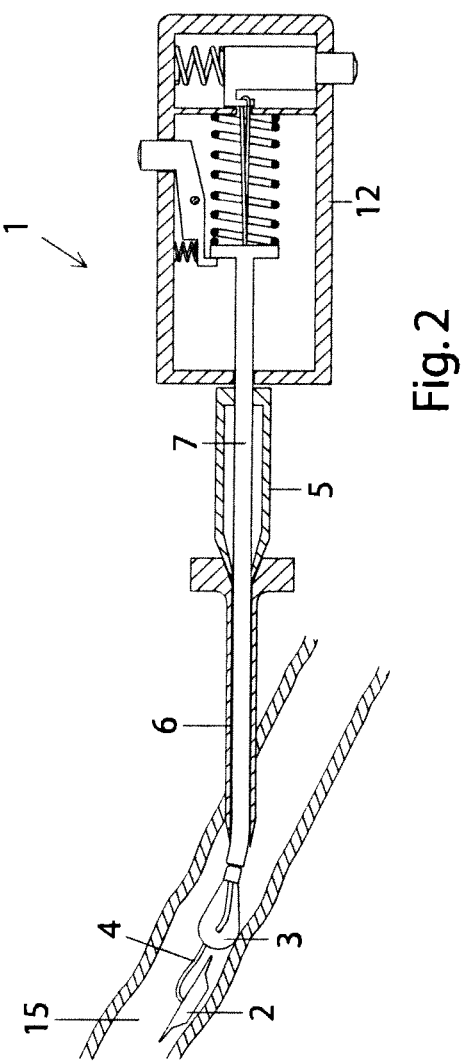
Figure 3:
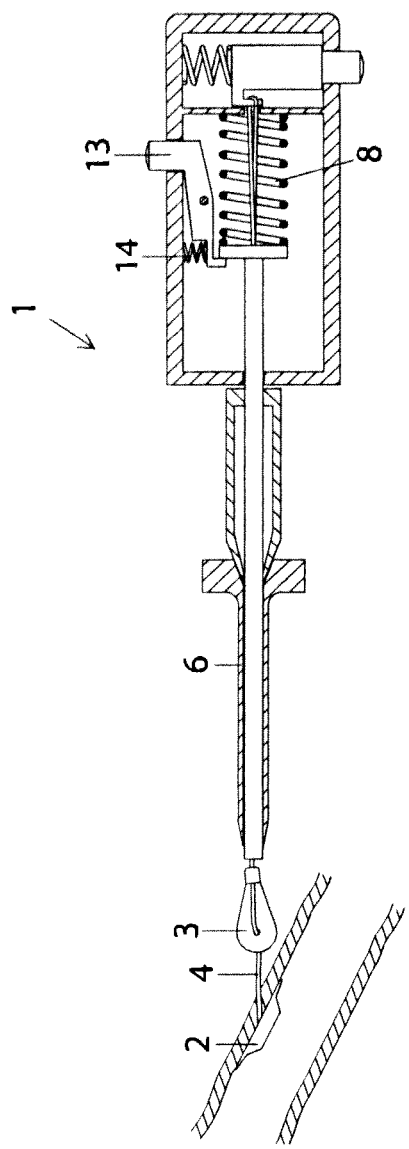

In a first step, illustrated in FIG. 2, the insertion tool is attached to the pre-placed introducer 6 and the closure device is advanced by the tamping tube 7 through the introducer 6 into a vessel 15 by advancing the proximal housing 12 towards the distal housing 5 of the insertion tool 1 (compare FIG. 1 and FIG. 2). In this embodiment, the tamping tube 7 acts as a pusher, however, it is also conceivable to provide a separate pusher. During the introduction, the inner member 2 can be in a folded configuration or a longitudinal position within the insertion tool 1. If the inner member 2 is initially folded, it is manipulated in such a way that it will unfold during insertion into the vessel when outside the introducer 6. In FIG. 2 both the inner and outer closure members 2, 3, connected by the filament 4, are initially deployed inside the vessel 15. Thereafter the insertion tool 1 and the pre-placed introducer 6 are retracted until the inner sealing disc 2 contacts the inner vessel wall, which is felt by the user as a resistance on the filament 4. This step is illustrated in FIG. 3. In this type of closure device, the outer member 3 is constructed so as to pass freely through the opening when retracting the insertion tool 1. Even though both closure members 2, 3 are illustrated as initially being deployed inside the vessel, it should be noted that it is also within the scope of the present invention to provide an insertion tool where an inner member is deployed inside the vessel and subsequently, after retraction of the assembly, an outer member is placed outside the vessel. The different possible types of closure assemblies have been discussed above.

Figure 4:
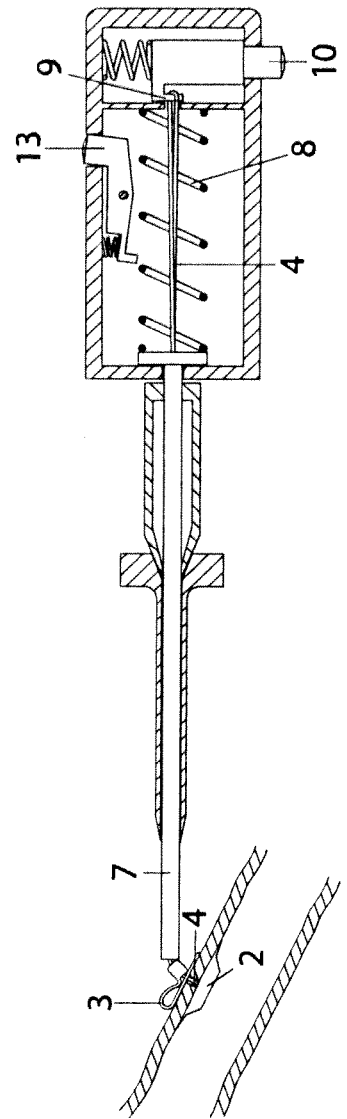

After deployment of the two closure members and retraction of the assembly to place the inner member against the puncture in the vessel wall, the closure device is ready for tamping. The user presses the tamping button 13 and thereby releases the tamping spring 8 from its compressed, i.e. energized, state (illustrated in FIG. 3), which then advances the tamping tube 7 to clamp the outer member 3 against the outer wall of the vessel (illustrated in FIG. 4). As mentioned earlier, the two closure members are constructed so that after tamping, the two members 2, 3 can be held together by any fastening mechanism.

In a subsequent step, the user presses release button 10, releasing the filament loop 4 from the hook 9 (see FIG. 5). The insertion tool can then be removed from the puncture site, leaving the closure members 2, 3 sandwiching the vessel puncture and the filament 4 protruding from the skin puncture. The closure members are preferably made of a resorbable material, so that they will be absorbed by the body as the puncture heals.

A further embodiment is illustrated in FIGS. 6 and 7. Similarly to the previously illustrated embodiment, closure members 22, 23 have been introduced through the introducer tube 26, by in this case, a tamping tube 27, into a vessel 35. This is achieved by the user inserting the insertion tool 20 into the introducer 26 and advancing the proximal housing 32, and subsequently retracting the entire assembly, i.e. the insertion tool 20 and the introducer 26, until the inner member 22 is against the vessel wall (FIG. 6). In this embodiment the continued retraction of the assembly will trigger release of the compressed spring 28 automatically, as illustrated in FIG. 7. Initially, as seen in FIG. 6, the tamping spring is held in a compressed, i.e. energized, state between the enlarged proximal end 39 of tamping tube 27 and an inner ledge 36 by a release fastening 33. As the assembly is retracted, the release fastening 33 will be forced to open by the interaction of a beveled surface 37, thereby pushing the tamping tube 27 forward with controlled force and speed, which in turn will position the outer closure member 23 at the vessel puncture to effectively sandwich the puncture by the two closure members 22, 23 (FIG. 7). Simultaneously, the movement forward of tamping tube 27 will release a filament loop 24 from a retaining hook 29. Consequently, the continued retraction of the insertion assembly will trigger tamping and release of the filament automatically. However, it is also within the scope of the present invention to provide automatic tamping as described above, and thereafter provide user-operated release of the filament, as described in connection with FIG. 5, or vice versa, i.e. user-operated release of the tamping spring and automatic release of the filament.

It should be noted that it is also within the scope of the invention to energize a tamping spring by extending the spring, and reversing the setup in the insertion tool. One such embodiment is illustrated in FIG. 8. The insertion tool 40 of this embodiment is similar to the first embodiment described in connection to FIG. 1, except that a tamping spring 48 is mounted and fastened at its distal end to a distal end 58 of proximal housing 52. Furthermore, the tamping spring 48 is mounted and fastened at its proximal end to an enlarged proximal end 59 of tamping tube 47. Prior to tamping, the tamping spring is held in an extended state, i.e. energized. Before the tamping step, the insertion tool 40 is maneuvered as described for previous embodiments, to place the inner member 42 inside the vessel 55 adjacent to the vessel puncture. On release of the tamping spring, by the user pressing on tamping button 53, the tamping tube 47 is advanced by the pulling force of the spring, effectively tamping the two closure members 42, 43 at the opening.

Figure 10:
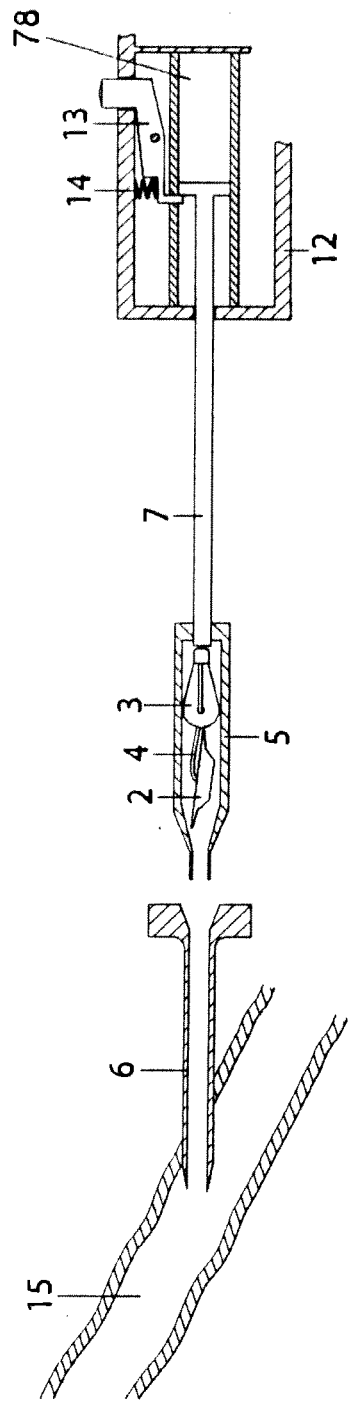
FIG. 10 illustrates a fifth embodiment of the present invention.
Figure 9:
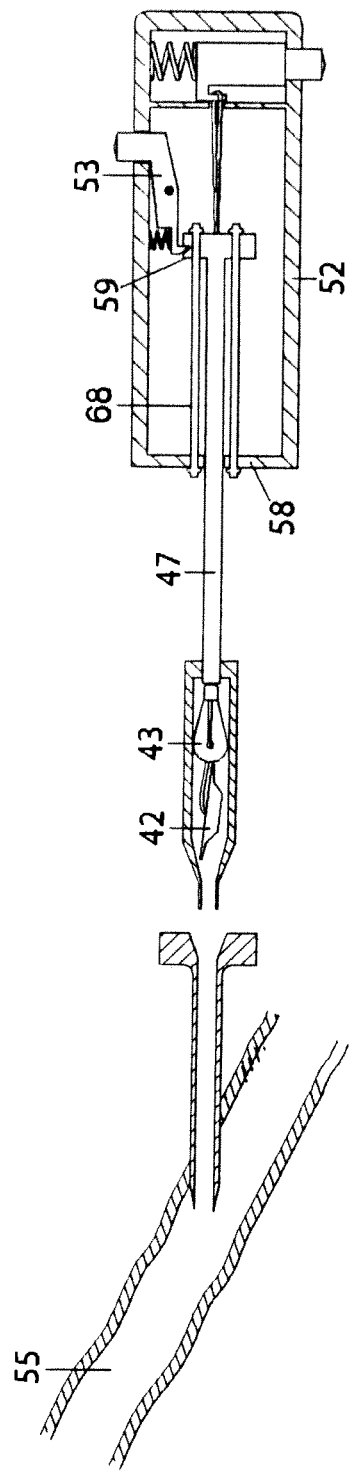
FIG. 9 illustrates a fourth embodiment of the present invention.

Notably, the energizing of a tamping force source, as used in connection with the tamping procedure in the embodiments described above, and in connection to using other tamping force sources, such as elastic, bands 68 in FIG. 9 or a pressurized gas container 78 in FIG. 10, can be performed any time before initiation of the tamping procedure. The energizing operation is separated from the closure procedure itself, and in particular from the tamping procedure, which commences when the two closure members are to be moved towards each other to achieve closure of the opening. The energizing of a tamping force source can be performed during manufacture of the device or by the user before initiation of the closure procedure, or before initiation of the tamping procedure itself. The loading of the tamping spring can be performed by a manual operation, e.g. pushing the tamping tube 7, 27, 47 proximally into the proximal housing 12, 32, 52, in order to snap the fastening mechanism 13, 33, 53 into the initial position. Another variation is to provide a separate plunger for loading of the spring. Similar mechanisms can be provided when using elastic bands or a pressurized gas container.

The tamping spring 8, 28 can be produced from any known material suitable for use in springs, including, but not limited to metals, such as steel or nitinol, and plastics. In particular, the spring, or other tamping force source, is designed to deliver a specific tamping force for tamping of the closure device. The required force is adapted to deliver a sufficient amount of force for tamping, while keeping potentially rupturing forces to a minimum. Therefore, the tamping force exerted by the tamping force source is preferably within the range of 5 N and 40 N, more preferably between 8 N and 12 N. It should be noted that the term tamping force is to be taken as the force exerted on the proximal closure member by the tamping tube at the final stages of tamping or sandwiching of the two closure members at the opening, and is opposed by the retaining member, .i.e. the filament in the embodiments above. If using e.g. a compressed spring, the initial force on release of the tamping mechanism will be higher than the final force, due to the nature of a spring, however, the final tamping force is preferably within the abovementioned range.

Although the present invention has been described with reference to specific embodiments it will be apparent for those skilled in the art that many variations and modifications can be performed within the scope of the invention as described in the specification and defined with reference to the claims below.

The invention claimed is:

1. An insertion tool for a medical device for closure of an opening in a wall of a bodily organ, the medical device comprising at least a first member and a second member, the insertion tool comprising:
    a tamping mechanism configured to bring together the first and second members on opposite sides of the wall,
    wherein the tamping mechanism comprises a housing, a fastener, a tamping member protruding from the housing, and a tamping force source attached to an inside of the housing,
    wherein the tamping force source is configured to be energized prior to initiation of a tamping procedure such that the energized tamping force source is configured to apply an application force to the tamping member while the tamping member is held in place by the fastener,
    wherein the tamping force source is configured to advance the tamping member away from the housing after actuation during the tamping procedure by releasing the fastener from the tamping member, and
    wherein the releasing of the fastener from the tamping member is configured to be triggered by retraction of the housing away from at least one of the first and second members.

2. The insertion tool according to claim 1, wherein the tamping force source is a spring, which is compressed upon energizing.

3. The insertion tool according to claim 1, wherein the tamping force source, upon energizing, is configured to be compressed between the tamping member and an internal surface while the tamping member is held by the fastener, and wherein the internal surface is slidable relative to the housing.

4. The insertion tool according to claim 1, wherein, while the tamping member is held by the fastener, the fastener is configured to slide relative to the housing during the retraction of the housing away from the at least one of the first and second members.

5. The insertion tool according to claim 4, wherein the release of the fastener from the tamping member is configured to be triggered when a surface of the fastener interacts with a beveled surface of the housing.

6. The insertion tool according to claim 1, wherein the tamping force source, when energized, is configured to deliver a set amount of tamping force when released.

7. The insertion tool according to claim 1, wherein the bodily organ is a blood vessel or a septal defect.

8. The insertion tool according to claim 1, further comprising a restraining member, wherein the restraining member is configured to hold on to a filament at an interior space of the housing during the tamping procedure and configured to automatically release the filament upon advancement of the tamping member away from the housing after actuation during the tamping procedure.

9. The insertion tool according to claim 1, wherein tamping force in the tamping force source, when energized, is between 5 N and 40 N.

10. The insertion tool according to claim 1, wherein energizing of the tamping force source is performable by a user prior to insertion of the medical device into the opening or during manufacture of the insertion tool.

11. The insertion tool according to claim 1, wherein the tamping mechanism is configured to bring together the first and second members on opposite sides of the wall by applying a tamping force to one of the first and second members while the other of the first and second members is retained in position.

12. A medical device for closure of an opening in a wall of a bodily organ, comprising:
    a first member;
    a second member;
    a filament; and
    an insertion tool comprising a tamping mechanism adapted to bring together the first and second members on opposite sides of the wall,
    wherein the tamping mechanism comprises a housing, a tamping member protruding from the housing, a fastener, and a tamping force source attached to the housing,
    wherein the tamping force source is configured to be energized prior to initiation of a tamping procedure such that the energized tamping force source is configured to apply an application force to the tamping member while the tamping member is held in place by the fastener,
    wherein the tamping force source is configured to advance the tamping member away from the housing after actuation during the tamping procedure by releasing the fastener from the tamping member, and
    wherein the fastener is configured to be released by retraction of the housing away from at least one of the first and second members.

13. The medical device according to claim 12, wherein the tamping force source, when energized, is configured to deliver a set amount of tamping force when the fastener is released.

14. The medical device according to claim 12, wherein the tamping force source is a spring, which is compressed upon energizing.

15. The medical device according to claim 12, wherein the bodily organ is a blood vessel or a septal defect.

16. The medical device according to claim 12, wherein the tamping mechanism is configured to bring together the first and second members on opposite sides of the wall by applying a tamping force to one of the first and second members while the other of the first and second members is retained in position.

17. The medical device according to claim 12, further comprising a restraining member, wherein the restraining member is configured to hold on to the filament at an interior space of the housing during the tamping procedure and configured to automatically release the filament upon advancement of the tamping member away from the housing after actuation during the tamping procedure.

18. The medical device according to claim 12, wherein the tamping force source, upon energizing, is configured to be compressed between the tamping member and an internal surface while the tamping member is held by the fastener.

19. The medical device according to claim 12, wherein, while the tamping member is held by the fastener, the fastener is configured to slide relative to the housing during the retraction of the housing away from the at least one of the first and second members.

20. The medical device according to claim 19, wherein the release of the fastener from the tamping member is configured to be triggered when a surface of the fastener interacts with a beveled surface of the housing.

21. A method for closing an opening in a wall of a bodily organ, comprising:
    placing first and second members on opposite sides of the wall, wherein the first and second members are connected via a filament to an insertion tool, wherein the insertion tool comprises a tamping mechanism that comprises a housing, a tamping member protruding from the housing, a fastener, and a tamping force source attached to the housing, wherein the tamping force source is energized such that the energized tamping force source applies an application force to the tamping member while the tamping member is held in place by the fastener;
    retracting the housing away from the first and second members such that the fastener is automatically released from the tamping member, and
    automatically advancing the tamping member away from the housing using the tamping force source after the automatic release of the fastener from the tamping member such that an application of a tamping force to one of the first and second members results while the other of the first and second members is retained in position such that the first and second members are brought together on the opposite sides of the wall.

22. The method according to claim 21, wherein the bodily organ is a blood vessel or a septal defect.

23. The method according to claim 21, further comprising:
    holding on to the filament at an interior space of the housing using a restraining member; and
    automatically releasing the filament from the restraining member upon automatic advancement of the tamping member away from the housing.

24. The method according to claim 21, wherein, during the retracting of the housing away from the first and second members, the tamping member is held by the fastener and the fastener slides relative to the housing, and
    wherein the releasing of the fastener from the tamping member is triggered when a surface of the fastener interacts with a beveled surface of the housing.

* * * * *